United States Patent
Fenchel et al.

(10) Patent No.: US 9,572,493 B2
(45) Date of Patent: Feb. 21, 2017

(54) METHOD FOR DISPLAYING SIGNAL VALUES OF A COMBINED MAGNETIC RESONANCE POSITRON EMISSION TOMOGRAPHY DEVICE AND A CORRESPONDINGLY EMBODIED MAGNETIC RESONANCE POSITRON EMISSION TOMOGRAPHY DEVICE

(71) Applicant: SIEMENS AKTIENGESELLSCHAFT, Munich (DE)

(72) Inventors: Matthias Fenchel, Erlangen (DE); Björn Heismann, Erlangen (DE); Kirstin Jattke, Nuremberg (DE); Ralf Ladebeck, Erlangen (DE); Sebastian Schmidt, Weisendorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 373 days.

(21) Appl. No.: 14/219,440

(22) Filed: Mar. 19, 2014

(65) Prior Publication Data

US 2014/0296697 A1    Oct. 2, 2014

(30) Foreign Application Priority Data

Mar. 26, 2013  (DE) .................... 10 2013 205 278

(51) Int. Cl.
| | | |
|---|---|---|
| *A61B 5/00* | (2006.01) | |
| *A61B 5/055* | (2006.01) | |
| *G01R 33/48* | (2006.01) | |

(52) U.S. Cl.
CPC ............ *A61B 5/0035* (2013.01); *A61B 5/055* (2013.01); *G01R 33/481* (2013.01)

(58) Field of Classification Search
CPC ...... A61B 5/0035; A61B 5/055; G01R 33/481
See application file for complete search history.

(56) References Cited

U.S. PATENT DOCUMENTS

| | | | | |
|---|---|---|---|---|
| 5,187,658 A | * | 2/1993 | Cline | .................. G06F 19/3437 324/306 |
| 5,490,516 A | | 2/1996 | Hutson | |
| 5,641,965 A | | 6/1997 | Barber | |

(Continued)

FOREIGN PATENT DOCUMENTS

| | | |
|---|---|---|
| CN | 101051387 A | 10/2007 |
| CN | 101719274 A | 6/2010 |
| CN | 102749602 | 10/2012 |
| DE | 102007037103 A1 | 2/2009 |

(Continued)

OTHER PUBLICATIONS

Malone et al., Attenuation Correction Methods Suitable for Brain Imaging with a PET/MRI Scanner: A Comparison of Tissue Atlas and Template Attenuation Map Approaches, J Nucl Med 2011; 52:1142-1149.*

(Continued)

*Primary Examiner* — Bo J Peng
(74) *Attorney, Agent, or Firm* — Harness, Dickey & Pierce, P.L.C.

(57) ABSTRACT

A method, a computer program product and a computer-readable storage medium are disclosed for displaying signal values of a combined magnetic resonance positron emission tomography device. In at least one embodiment, the spatial correspondence of signal values, which result from a magnetic resonance measurement, and of signal values, which result from a positron emission tomography measurement, are used and the corresponding signal values are arranged in matrix form and displayed graphically as a multi-dimensional scatter plot.

20 Claims, 2 Drawing Sheets

(56) References Cited

U.S. PATENT DOCUMENTS

| | | |
|---|---|---|
| 2003/0128801 A1 | 7/2003 | Eisenberg |
| 2004/0264752 A1 | 12/2004 | Alyassin |
| 2005/0031202 A1 | 2/2005 | Accomazzi |
| 2006/0250133 A1 | 11/2006 | Krieg et al. |
| 2007/0223794 A1 | 9/2007 | Preiss et al. |
| 2008/0310698 A1 | 12/2008 | Boeing |
| 2009/0048507 A1 | 2/2009 | Feiweier |
| 2010/0106004 A1 | 4/2010 | Harvey |
| 2010/0254584 A1 | 10/2010 | Gulsun |
| 2011/0160543 A1 | 6/2011 | Mikhno |
| 2012/0184843 A1 | 7/2012 | Chen |
| 2012/0268118 A1 | 10/2012 | Fenchel et al. |
| 2013/0004044 A1 | 1/2013 | Galban |

FOREIGN PATENT DOCUMENTS

| | | |
|---|---|---|
| JP | 2006280929 A | 10/2006 |
| JP | 2010512907 | 4/2010 |
| WO | WO 2012147011 A1 | 11/2012 |

OTHER PUBLICATIONS

Hofmann et al., MRI-Based Attenuation Correction for PET/MRI: A Novel Approach Combining Pattern Recognition and Atlas Registration, J Nucl Med 2008; 49:1875-1883.*

Keereman et al., MRI-Based Attenuation Correction for PET/MRI Using Ultrashort Echo Time Sequences, The Journal of Nuclear Medicine, vol. 51, No. 5, May 2010.*

Ashburner et al., Human Brain Function, 2nd Edition, Chapter 2, Rigid Body Registration http://www.fil.ion.ucl.ac.uk/spm/doc/books/hbf2/, Oct. 18, 2005.*

Gulsun M. A. et al: "MR ONCO-TREAT: A New Tool for Volumetric and Functional Analysis of Hepatic Tumors Monitored with Multi-Modal MRI", Proc. Intl. Soc. Mag. Reson. Med., 17 (2009), p. 2876; 2009.

German Office action for DE102013205278.2 dated Dec. 13, 2013.

German Priority Document 102013205278.2 dated Mar. 26, 2013.

Maes, Frederik et al. "Multimodality Image Registration by Maximization of Mutual Information" IEEE Transactions on Medical Imaging, vol. 16, No. 2, Apr. 1997; pp. 187-198.

Zaidi, H. et al. "Design and performance evaluation of a whole-body Ingenuity TF PET—MRI system" Phys Med Biol. May 21, 2011; vol. 56 No. (10); pp. 3091-3106.

Delso, Gaspar et al. "Performance Measurements of the Siemens mMR Integrated Whole-Body PET/MR Scanner" The Journal of Nuclear Medicine; vol. 52; No. 12; Dec. 2011; pp. 1914-1922.

Chinese Office Action and English translation thereof dated Nov. 2, 2015.

Korean Office Action dated Jan. 4, 2016.

* cited by examiner

METHOD FOR DISPLAYING SIGNAL VALUES OF A COMBINED MAGNETIC RESONANCE POSITRON EMISSION TOMOGRAPHY DEVICE AND A CORRESPONDINGLY EMBODIED MAGNETIC RESONANCE POSITRON EMISSION TOMOGRAPHY DEVICE

PRIORITY STATEMENT

The present application hereby claims priority under 35 U.S.C. §119 to German patent application number DE 102013205278.2 filed Mar. 26, 2013, the entire contents of which are hereby incorporated herein by reference.

FIELD

At least one embodiment of present invention generally relates to a method for displaying signal values of a combined magnetic resonance positron emission tomography device; a corresponding computer program product, which allows for the execution of a method; an electronically readable data carrier and/or a combined magnetic resonance positron emission tomography device.

BACKGROUND

Imaging methods for displaying examination objects, in particular for determining material properties, the material arrangement and expansion or suchlike are widespread in particular in terms of their medical application.

The image data of various known medical examination facilities allows for different conclusions. While x-ray-based image data allows for statements to be made about the attenuation coefficients of the imaged examination object, magnetic resonance tomography enables knowledge to be obtained about the proton density or the density of the respectively excited cores, relaxation parameters and other variables. Positron emission tomography by contrast enables functional imaging, without reaching the local resolution of the magnetic resonance tomography for instance. There is therefore the need for combined medical examination facilities, which allow for the receiving of image data from a number of examination facilities, in order ultimately to acquire fused image data. Improved information can then be derived from this fused image data for diagnosis purposes in particular than when taking just singular image data into account, in other words image data from a single examination facility.

Magnetic resonance tomography (MRT) is an imaging method, which allows for the high resolution generation of sectional images of living organisms, such as humans. The patient is positioned in a homogeneous magnetic field B0. With gradient coils, the outer magnetic field in the FOV (field of view) is modified such that a body layer is selected on the one hand and a local encoding of the generated MR signals takes place on the other hand. With the subsequent reconstruction of the MR signals for instance by way of Fourier transformation, an image of the selected layer is produced, which is used for medical diagnostics. The generation and detection of MR signals takes place with a high frequency system, which includes a transmit antenna, which radiates HF excitation pulses into the patient, and a receive antenna, which detects the emitted HF resonance signals and forwards the same for image reconstruction purposes. By selecting a suitable pulse sequence, such as a spin echo sequence or a gradient echo sequence, and the sequence parameters associated therewith, the contrast of MR images can be varied considerably depending on the diagnostic task description. The MRT images body structures and accordingly represents a structural imaging method.

Positron emission tomography (PET) is a widespread method for functional imaging. During an examination, a weak radioactive substance is administered to an examination person, the distribution of which in the organism is made visible by way of PET. As a result, biochemical and physiological functions of the organism can be mapped. Molecules are used here as radiopharmaceuticals, said molecules being marked with a radionuclide which emits the positrons. The high-energy photons produced during the annihilation of the positron with an electron in the body of the examined person, which are emitted at an angle of 180° relative to one another, are detected with a plurality of detectors arranged in an annular fashion about the examination person. Only coincidental events, which were recorded with two opposing detectors, are evaluated in each instance. The spatial distribution of the radiopharmaceutical in the inside of the body is concluded from the registered coincidental decay events and a series of sectional images is calculated. The image reconstruction can take place in such cases with a filtered back projection or an iteration method, wherein the spatial resolution generally remains inferior to the resolution of conventional computed tomography (CT) or magnetic resonance tomography systems.

SUMMARY

At least one embodiment of the invention provides a suitable output of signal values of a combined magnetic resonance positron emission tomography device.

A method is disclosed in at least one embodiment. A combined magnetic resonance positron emission tomography device is disclosed in at least one embodiment. A computer program product is disclosed in at least one embodiment. And a computer-readable storage medium is disclosed in at least one embodiment. Advantageous embodiments of the invention are specified in the respective back-related subclaims.

At least one embodiment of the invention uses the spatial correspondence of signal values obtained following an image registration, said correspondence resulting from a magnetic resonance measurement and of signal values which result from a positron emission tomography measurement. The corresponding signal values are arranged in matrix form and are shown graphically as a multi-dimensional scatter plot (also scatter diagram).

In at least one embodiment, a method is provided, with which the signal values of a combined magnetic resonance positron emission tomography device are shown, and includes at least the following:

assigning a first image data record with signal parameters which result from a magnetic resonance measurement to a second image data record with signal parameters which result from a positron emission tomography measurement;

assigning at least one signal parameter of the first image data record to at least one signal parameter of the second image data record in the form of an n tuple, wherein n specifies the number of assigned signal parameters and wherein the n tuple specifies spatially corresponding signal values; and outputting an n-dimensional scatter plot by displaying all n tuples, wherein a coordinates axis is assigned to each signal parameter.

Within the scope of at least one embodiment of the present invention, a combined magnetic resonance positron emission tomography device is also provided to display signal values. In such cases, the combined magnetic resonance positron emission tomography device includes a detection unit, a processing unit, a control facility and an output unit and is configured to implement at least the following:

assigning a first image data record with signal parameters which result from a magnetic resonance measurement to a second image data record with signal parameters which result from a positron emission tomography measurement, by way of the detection unit;

assigning at least one signal parameter of the first image data record to at least one signal parameter of the second image data record in the form of an n tuple, wherein n specifies the number of assigned signal parameters and wherein the n tuple specifies spatially corresponding signal values, by way of the processing unit; and outputting an n-dimensional scatter plot by displaying all n tuples, wherein a coordinates axis is assigned to each signal parameter, by way of the output unit.

Furthermore, at least one embodiment of the present invention describes a computer program product, in particular a computer program or software, which can be loaded into a memory of a programmable controller or a computing unit or a combined magnetic resonance positron emission tomography device. With this computer program product, all or various previously described embodiments of the inventive method can be executed, if the computer program product runs in the controller or control facility of the combined magnetic resonance positron emission tomography device. In such cases the computer program product requires possible program segments/modules, e.g. libraries and auxiliary functions, in order to realize the corresponding embodiments of the method. In other words, a computer program or a software is in particular to be protected with the claim focusing on the computer program product, with which one of the above-described embodiments of the inventive method can be executed or which execute this embodiment. In such cases, the software may be a source code, which must still be compiled and bound or which only has to be interpreted, or an executable software code, which is to be loaded for execution purposes into the corresponding computing unit.

Furthermore, at least one embodiment of the present invention relates to a computer-readable storage medium, e.g. a DVD, a magnetic tape or a USB stick, on which electronically readable control information, in particular software, is stored. If this control information is read from the data carrier and stored in a controller or computing unit of a combined magnetic resonance positron emission tomography device, all inventive embodiments of the previously described method can be implemented.

BRIEF DESCRIPTION OF THE DRAWINGS

The invention is described and explained in more detail below with the aid of the example embodiments displayed in the Figures.
in which.

DETAILED DESCRIPTION OF THE EXAMPLE EMBODIMENTS

Figure 1:
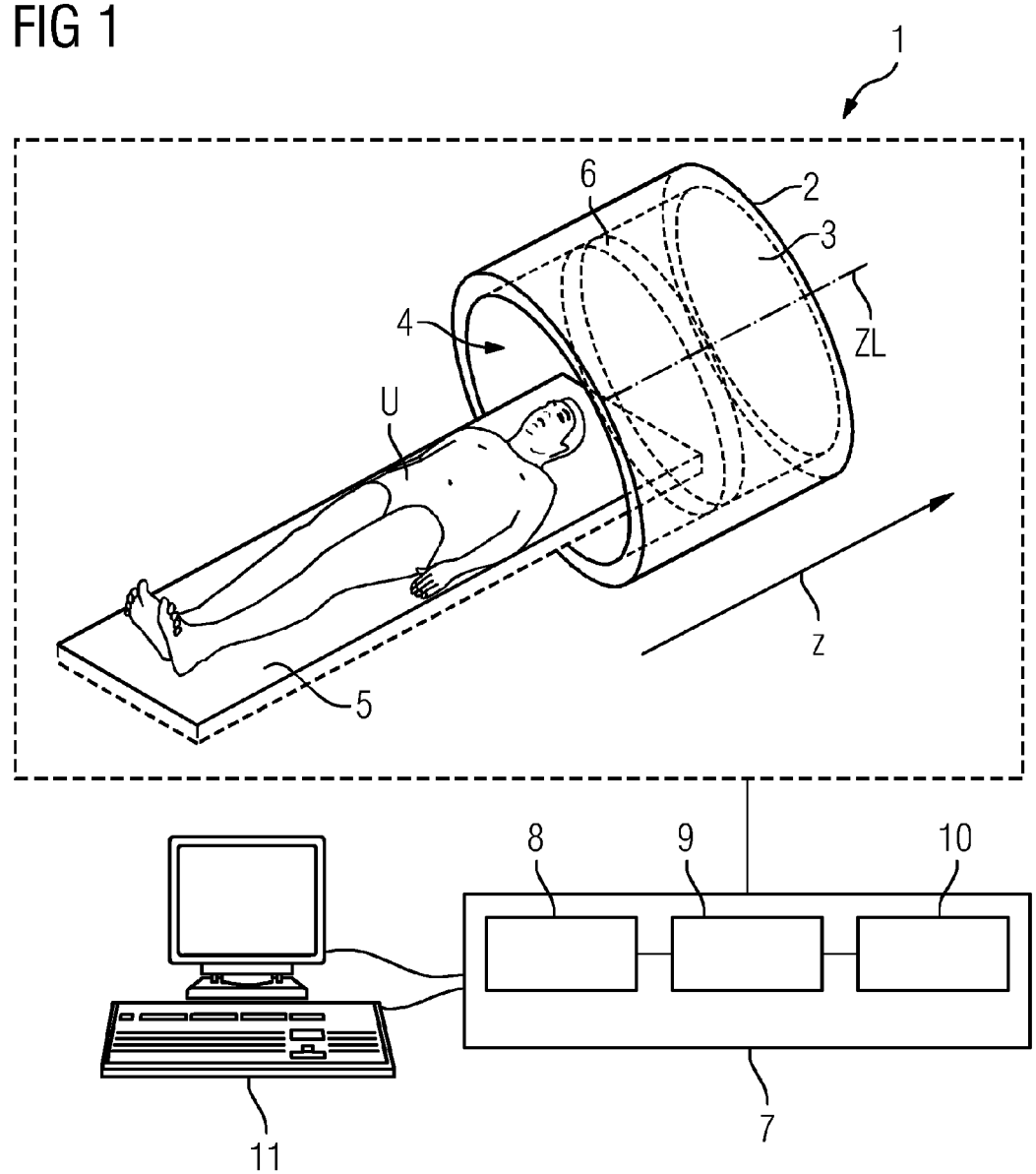
FIG. 1 shows a schematic representation of an embodiment of an inventive combined magnetic resonance positron emission tomography device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In at least one embodiment, a method is provided, with which the signal values of a combined magnetic resonance positron emission tomography device are shown, and includes at least the following:

assigning a first image data record with signal parameters which result from a magnetic resonance measurement to a second image data record with signal parameters which result from a positron emission tomography measurement;

assigning at least one signal parameter of the first image data record to at least one signal parameter of the second image data record in the form of an n tuple, wherein n specifies the number of assigned signal parameters and wherein the n tuple specifies spatially corresponding signal values; and outputting an n-dimensional scatter plot by displaying all n tuples, wherein a coordinates axis is assigned to each signal parameter.

The scatter plot generated in at least one embodiment of the inventive manner allows for a superimposed display of image information from a magnetic resonance measurement and a positron emission tomography measurement. Image data records which display the same anatomical structure in a different manner can be compared directly with one another. Differences for instance in the contrast values are thus visualized even more clearly.

Examples of signal parameters which result from a magnetic resonance measurement are inter alia the apparent diffusion coefficient (ADC), which specifies the self-diffusion of water in tissue fluid, the T2-weighted intensity, the T1-weighted intensity, the proton density, the T1-relaxation time, the T2-relaxation time, the susceptibility, the perfusion (e.g. ASL (arterial spin label) signal intensity or contrast agent enhancement), the water content, the fat content or the content of other signal-emitting atomic nuclei (such as phosphorus, natrium, fluoride etc.).

Examples of signal parameters which result from a positron emission tomography measurement are inter alia the SUV value (standardized uptake value), the regional radioactivity concentrations quantified, the attenuation-corrected PET intensity or the uncorrected PET intensity.

The n-tuples can be realized as a matrix, they can however also inter alia, but not exclusively, be realized as a list of lists or as an array.

In a preferred embodiment, precisely one signal parameter of the first image data record is assigned to precisely one signal parameter of the second image data record, so that a two-dimensional matrix of signal values or pixels is produced and a two-dimensional scatter plot of the corresponding signal values or pixel values is output. This allows for a simple, direct comparison of two spatially correlated signal parameters.

In an advantageous embodiment, precisely one signal parameter of the first image data record is assigned to precisely two signal parameters of the second image data record or precisely two signal parameters of the first image data record are assigned to precisely one signal parameter of the first image data record, so that a two-dimensional matrix of signal values or voxel is produced and a three-dimensional scatter plot of the corresponding signal values or voxels values is output. An intuitive comparison of spatially correlated signal parameters is also possible in this three-dimensional display.

In a further embodiment, the image data record of the magnetic resonance measurement is detected in a shared time window with the image data record of the positron emission tomography measurement. A temporal correlation is thus also achieved in addition to the spatial correlation which is produced by the first method step (often also referred to as image registration). For an optimal temporal correlation, the shared time window is to be selected to be sufficiently small that precisely two image recordings are possible with the two imaging methods. Artifacts, which result on account of large temporal distances between the image recordings, can be minimized.

An inventive embodiment contains the use of a correction method on at least one image data record, either prior to or after the first method step. Further artifacts can thus be minimized. Attenuation corrections of the PET data, distortion corrections of the MR data, movement corrections or partial volume corrections are taken into consideration as correction methods for instance.

A further inventive embodiment provides that a selection of the n-tuples displayed in the scatter plot takes place by way of at least one selection criterion and that at least one selection device for selecting at least one recorded area is made available to a user for selection purposes. As a result, it is possible to select directly significant image regions and thus to highlight regions with special contrast ratios for instance.

In an advantageous embodiment, the at least one selection device includes a geometric shape. Ellipse, rectangles, triangles, squares or pyramids can be considered as geometric shapes, with which corresponding geometric regions can be marked particularly easily in the scatter plot. These regions can be scatter plots of various sizes for instance.

In an advantageous embodiment, the at least one selection device includes a separation function. Straight lines, polynomials, exponential functions or trigonometric functions are taken into account as separation functions for instance, with which different regions, such as point clouds in scatter plots, can be particularly easily separated from one another.

In a further embodiment, the data within the selected area is arranged in a different manner relative to data outside of the selected area. This can take place for instance such that the marked region of n tuples is displayed in a color which differs from the region of n tuples which was not marked. As a result, a relevant image region can be rapidly and directly detected by an observer.

In an example embodiment, the at least one selection criterion results in a selection of image data in the first and/or second image data record. As a result, the selected region is also immediately highlighted in the anatomical image data record, so that it is easily apparent to which regions in the image data records the selected n-tuples in the scatter plot correspond.

In a further embodiment, at least one selection criterion is applied to at least one image data record, which is detected in a further time window. In this way, temporal changes can be traced for instance in the image data records. As a result, relevant changes in an image region can be rapidly and directly detected by an observer.

In a further embodiment, image data and/or signal values of the first and/or second image data, which are included in the selected area when superimposing the first image data record with the second image data record, are weighted and can thus influence the superimposition. In this way, the selected area can be extracted for instance from the scatter plot from the image data record with signal values which result from a magnetic resonance measurement, and the remaining area from the image data record with signal values which result from a positron emission tomography measurement. The reverse procedure can also be realized. A weighting can also include the forming of a differential image, within the scope of which, signal values which result from a magnetic resonance measurement, and signal values which result from a positron emission tomography measurement, are multiplied with factors, such as for instance with real numbers. As a result, image parameters, such as for instance different contrasts, can be optimized.

In a preferred embodiment, the at least one area selected by the user is used for a segmentation in the first and/or section image data record. By assuming that selected, significant regions represent a particular part of the underlying image data records to be highlighted, it is in some instances advantageous to segment this region. To this end, information from the scatter plot, e.g. bounding edges or curves, can be used in order to describe the associated area. This results in a quicker workflow, above all in routines which still require a segmentation. In addition, irregularities in the image data records can be identified directly.

Within the scope of at least one embodiment of the present invention, a combined magnetic resonance positron emission tomography device is also provided to display signal values. In such cases, the combined magnetic resonance positron emission tomography device includes a detection unit, a processing unit, a control facility and an output unit and is configured to implement at least the following:

assigning a first image data record with signal parameters which result from a magnetic resonance measurement to a second image data record with signal parameters which result from a positron emission tomography measurement, by way of the detection unit;

assigning at least one signal parameter of the first image data record to at least one signal parameter of the second image data record in the form of an n tuple, wherein n specifies the number of assigned signal parameters and wherein the n tuple specifies spatially corresponding signal values, by way of the processing unit; and outputting an n-dimensional scatter plot by displaying all n tuples, wherein a coordinates axis is assigned to each signal parameter, by way of the output unit.

Furthermore, at least one embodiment of the present invention describes a computer program product, in particular a computer program or software, which can be loaded into a memory of a programmable controller or a computing unit or a combined magnetic resonance positron emission tomography device. With this computer program product, all or various previously described embodiments of the inventive method can be executed, if the computer program product runs in the controller or control facility of the combined magnetic resonance positron emission tomography device. In such cases the computer program product requires possible program segments/modules, e.g. libraries and auxiliary functions, in order to realize the corresponding embodiments of the method. In other words, a computer program or a software is in particular to be protected with the claim focusing on the computer program product, with which one of the above-described embodiments of the inventive method can be executed or which execute this embodiment. In such cases, the software may be a source code, which must still be compiled and bound or which only has to be interpreted, or an executable software code, which is to be loaded for execution purposes into the corresponding computing unit.

Furthermore, at least one embodiment of the present invention relates to a computer-readable storage medium, e.g. a DVD, a magnetic tape or a USB stick, on which electronically readable control information, in particular software, is stored. If this control information is read from the data carrier and stored in a controller or computing unit of a combined magnetic resonance positron emission tomography device, all inventive embodiments of the previously described method can be implemented.

The advantages of embodiments of the inventively combined magnetic resonance positron emission tomography device, of embodiments of the inventive computer program product and of embodiments of the inventive computer-readable storage medium correspond substantially to the advantages of embodiments of the inventive method, which are cited in detail above. Features, advantages or alternative embodiments mentioned here are likewise also to be transferred to the other claimed subject matters and vice versa. In other words, the objective claims, which focus on a device for instance, can also be embodied with the features which are described or claimed in conjunction with a method. The corresponding functional features of the method are embodied here by corresponding objective modules, in particular by hardware modules.

FIG. 1 shows a schematic representation of an embodiment of an inventive combined magnetic resonance positron emission tomography device 1. The device includes a magnetic resonance imaging facility 2 and an PET imaging facility 3. Instead of the PET imaging facility 3, it is similarly conceivable to use another radionuclide imaging facility, like for instance a SPECT imaging facility. In addition to further components known to the person skilled in the art, the PET imaging facility 3 comprises a radiation detector unit 6 for positron recombination radiation with an energy of approximately 511 keV. The preferred embodiment in such cases includes scintillation crystals, which convert the high-energy PET radiation into photons which can be detected by photodiodes. With annihilation of a positron and electron (pair forming), two photons are generated with an energy of respectively approximately 511 keV, the trajectories of which create an angle of 180°. With the aid of the PET radiation detector 6, these photon pairs can be measured coincidentally, so that a back calculation of the trajectories and as a result a spatial determination of the source of the detected photon pairs is possible in an examination object U. This back-calculation allows for the determination of the spatial concentration of the tracer in the examination object U. In conjunction with the image information of the magnetic resonance imaging facility 2, such high-resolution, detailed combination images of the examination object U can be acquired, in which the tracer concentration can be identified in its anatomical field.

In the example embodiment, the radiation detector unit 6 is arranged annularly around a center axis ZL of a measurement space 4 of the combined magnetic resonance positron emission tomography device 1, which is essentially oriented in parallel with a spatial direction z, which corresponds to the alignment of a basic magnetic field of the combined magnetic resonance positron emission tomography device 1. The annular arrangement allows for an essentially identical distance of an examination object U arranged in the center or in the region of the center axis ZL of the measurement space 2 relative to all image points of the radiation detector unit 6. In order to position the examination object U, a patient couch 5 is arranged in the measurement space 2, with the aid of which the examination object U can be moved along the center axis ZL.

For magnetic resonance imaging, the measurement space 2 of the combined magnetic resonance positron emission tomography device 1 is surrounded by a superconducting basic field magnet of the magnetic resonance imaging facility 2, which generates a homogeneous basic magnetic field in the measurement space 2, which is oriented in the z-direction. The current measurement region of the examination object U is to lie within a homogeneity volume of the basic magnetic field.

Furthermore, the magnetic resonance image facility 2 has a transmit coil, in most instances a body coil installed permanently in the device around the measurement space, with which high frequency signals can be emitted with the desired magnetic resonance frequency, in order to excite the spins in a specific region of the examination object. Furthermore, the magnetic resonance imaging facility 2 includes a gradient coil system, with the aid of which the local resolution of an item of magnetic resonance image information can be achieved. The magnetic resonance image information, i.e. the magnetic resonance signals excited in the examination object, are detected here in most instances with the aid of local coils. Furthermore, the local coils can also be embodied to generate high-frequency fields, which are used to excite the spins, and/or the developing magnetic resonance signals can be detected with the body coil.

The image processing for the superimposed magnetic resonance and positron emission tomography image display takes place in a computing unit 7, which, in this example embodiment, includes a detection unit 8, a processing unit 9 and a control facility 10.

Figure 2:
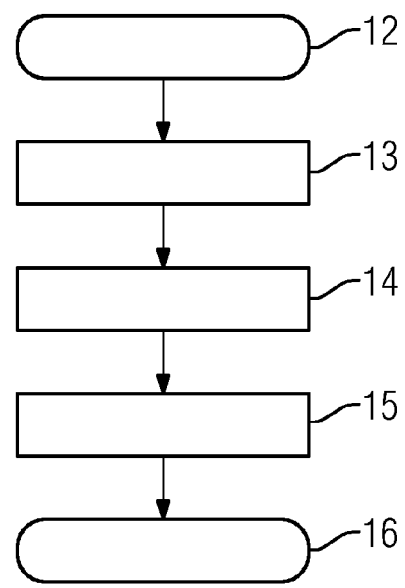
FIG. 2 shows a flow chart of a method according to an embodiment of the invention and
FIG. 3 shows a schematic representation of the assignment of signal values to 2 tuples.

FIG. 2 shows a flow chart of a method according to an embodiment of the invention. The method includes the method steps 12 to 16, wherein, when describing the method steps 12 to 16, the description parts including the corresponding reference characters introduced in conjunction with FIG. 1 are used.

In the method step 12, the display of signal values of a combined magnetic resonance positron emission tomography device 1 is started and a first image data record with signal values which result from a magnetic resonance measurements, and a second image data record with signal values which result from a positron emission tomography measurement are detected. The image data record of the magnetic resonance measurement can advantageously be detected in a shared time window with the image data record of the positron emission tomography measurement. Similarly, a correction method can be applied to at least one image data record.

In method step 13, the first image data record with signal values which result from a magnetic resonance measurement is assigned to the second image data record with signal values which result from a positron emission tomography measurement, by way of the detection unit 8 of the combined magnetic resonance positron emission tomography device 1.

In method step 13, precisely one signal parameter of the first image data record can also be assigned to precisely one signal parameter of the second image data record in the form of a two-dimensional matrix of pixels and a two-dimensional scatter plot 17 of the corresponding pixel values can be output. It is also conceivable for precisely one signal parameter of the first image data record to be assigned precisely two signal parameters of the second image data record or wherein precisely two signal parameters of the first image data record is assigned to precisely one signal parameter of the second image data record in the form of a three-dimensional matrix of voxels and that a three-dimensional scatter plot (17) of the corresponding voxel values is output.

In method step 14, at least one signal parameter of the first image data record is assigned to at least one signal parameter of the second image data record in the form of an n-tuple 20 by way of the processing unit 9 of the combined magnetic resonance positron emission tomography device 1, wherein n specifies the number of assigned signal parameters and the n-tuples 20 specify spatially corresponding signal values and in method step 15, an n-dimensional scatter plot 17 is output finally by way of the output unit 11 of the combined magnetic resonance positron emission tomography device 1 by representing the n-tuple 20, wherein a coordinate axis is assigned to each signal parameter. Method step 16 identifies the end of the signal value representation.

In method step 15, a selection of the n-tuples 20 shown in the scatter plot 17 can also be selected by way of at least one selection criterion and a selection device for selecting at least one identified area can be made available to a user for selection purposes. In such cases the at least one selection device can include a geometric form 18 or a separation function 19. The data within the selected area can be arranged in a different manner to the data outside of the selected area and the at least one selection criterion can lead to a selection of image data in the first and/or second image data record. It is likewise possible that the at least one selection criterion is applied to at least one image data record, which is detected in a further time window.

In method step 15, image data and/or signal values of the first and/or second image data record, which are included in the selected area when superimposing the first image data record with the second image data record, are weighted and it is possible for the at least one area selected by the user to be used for a segmentation in the first and/or second image data record.

Figure 3:
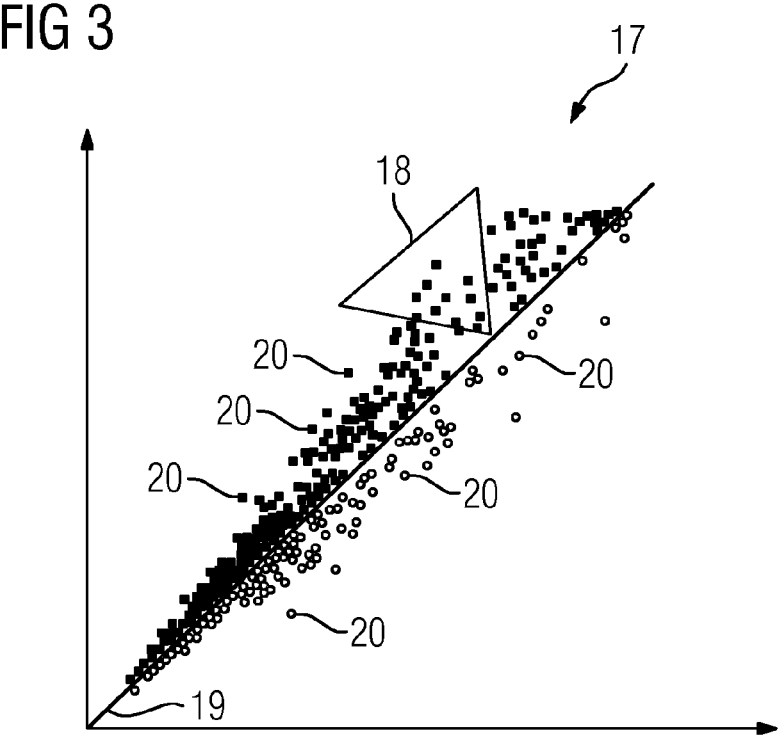

FIG. 3 shows a schematic representation of the assignment 14 of signal values to 2 tuples 20. The 2 tuples 20 specify spatially corresponding signal values. Precisely one signal value of the first image data record is assigned to precisely one signal value of the second image data record in the form of a two-dimensional matrix of pixels.

Furthermore, a selection takes place of the 2 tuples 20 shown in the scatter plot 17, wherein the selection device includes a geometric shape 18, here a triangle. Geometric shapes 18 include for instance ellipses, rectangles, squares or pyramids etc., with which corresponding geometric regions in the scatter plot can be marked particularly easily.

The selection device can however also include a separation function 19, here for instance in the form of a straight line. Polynomials, exponential functions or trigonometric functions etc. are considered as separation functions 19 for instance, with which different regions, such as point clouds in scatter plots, can be particularly easily separated from one another.

The 2-tuples 20 in the area selected by the selection device can be shown for instance in a color which differs from the region of 2-tuples 20, which does not correspond to the selected area. This area can then preferably also be highlighted in the underlying anatomical image data records, so that it is readily apparent to which regions in the image data records the selected 2 tuples 20 in the scatter plot correspond. With the images of differential images, image parameters, such as for instance different contrasts, can preferably also be optimized.

To summarize, embodiments of the invention relate to a method, a computer program product and a computer-readable storage medium for displaying signal values of a combined magnetic resonance positron emission tomography device. In such cases the spatial correspondence of signal values which result from a magnetic resonance measurement and of signal values which result from a positron emission tomography measurement is used, and the corresponding signal values are arranged in matrix form and displayed graphically as a multi-dimensional scatter plot.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. A method for displaying signal values of a combined magnetic resonance positron emission tomography device, the method comprising:
   assigning a first image data record with signal parameters which result from a magnetic resonance measurement to a second image data record with signal parameters which result from a positron emission tomography measurement;
   assigning at least one signal parameter of the first image data record to at least one signal parameter of the second image data record in the form of an n tuple, wherein n is greater than one and specifies a number of assigned signal parameters and wherein the n tuple specifies spatially corresponding signal values of the first image data and the second image data; and
   outputting an n-dimensional scatter plot by displaying all n tuples, wherein a coordinates axis is assigned to each of the signal parameters.

2. The method of claim 1, wherein one signal parameter of the first image data record is assigned to one signal parameter of the second image data record, so that a two-dimensional matrix of signal values is produced and wherein a two-dimensional scatter plot of the corresponding signal values is output.

3. The method of claim 2, wherein, by way of at least one selection criterion, a selection of the n-tuples shown in the scatter plot takes place and wherein at least one selection device, configured to select at least one identified area is made available to a user for selection purposes.

4. The method of claim 1, wherein one signal parameter of the first image data record is assigned to two signal parameters of the second image data record, or wherein two signal parameters of the first image data record are assigned to one signal parameter of the second image data record, so that a two-dimensional matrix of signal values is produced and wherein a three-dimensional scatter plot of the corresponding signal values is output.

5. The method of claim 4, wherein, by way of at least one selection criterion, a selection of the n-tuples shown in the scatter plot takes place and wherein at least one selection device, configured to select at least one identified area is made available to a user for selection purposes.

6. The method of claim 1, wherein the image data record of the magnetic resonance measurement is detected during at least a portion of detecting the image data record of the positron emission tomography measurement.

7. The method of claim 1, wherein a correction method is applied prior to or after the assigning of the first image data record.

8. The method of claim 1, wherein, by way of at least one selection criterion, a selection of the n-tuples shown in the scatter plot takes place and wherein at least one selection device, configured to select at least one identified area is made available to a user for selection purposes.

9. The method of claim 8, wherein the at least one selection device includes a geometric shape.

10. The method of claim 8, wherein the at least one selection device includes a separation function.

11. The method of claim 8, wherein the data within the selected area is arranged in a different manner to data outside of the selected area.

12. The method of claim 8, wherein the at least one selection criterion leads to a selection of image data in at least one of the first and second image data record.

13. The method of claim 8, wherein at least one selection criterion is applied to at least one image data record, detected in a further time window.

14. The method of claim 8, wherein at least one of image data and signal values of at least one of the first and second image data, included in the selected area when superimposing the first image data record with the second image data record, are weighted.

15. The method of claim 8, wherein the at least one area selected by the user is used for a segmentation in at least one of the first and second image data record.

16. A combined magnetic resonance positron emission tomography device for displaying signal values, comprising:
a detection unit;
a processing unit;
a control facility; and
an output unit, wherein
the detection unit is configured to assign a first image data record with signal parameters, which result from a magnetic resonance measurement, to a second image data record with signal parameters, which result from a positron emission tomography measurement,
the processing unit is configured to assign at least one signal parameter of the first image data record to at least one signal parameter of the second image data record in the form of an n tuple, wherein n is greater than one and specifies the number of assigned signal parameters and wherein the n tuple specifies spatially corresponding signal values of the first image data and the second image data, and
the output unit is configured to output an n-dimensional scatter plot by displaying all n tuples, wherein a coordinates axis is assigned to each signal parameter.

17. A non-transitory computer program product, including a program loadable directly into a memory of a programmable control facility of a combined magnetic resonance positron emission tomography device, the program including program segments to execute the method of claim 1 upon the program being run in the control facility of the combined magnetic resonance positron emission tomography device.

18. A non-transitory electronically readable data carrier including electronically readable control information stored thereupon, configured such that when using the data carrier in a control facility of a combined magnetic resonance positron emission tomography device, it is configured to implement the method of claim 1.

19. A non-transitory computer program product, including a program loadable directly into a memory of a programmable control facility of a combined magnetic resonance positron emission tomography device, the program including program segments to execute the method of claim 2 upon the program being run in the control facility of the combined magnetic resonance positron emission tomography device.

20. A non-transitory computer program product, including a program loadable directly into a memory of a programmable control facility of a combined magnetic resonance positron emission tomography device, the program including program segments to execute the method of claim 4 upon the program being run in the control facility of the combined magnetic resonance positron emission tomography device.

* * * * *